(12) United States Patent
Schneider (10) Patent No.: US 12,290,116 B2
(45) Date of Patent: May 6, 2025

(54) ANTIMICROBIAL UV-C EMITTING COMPOSITION FOR MASKS AND RELATED DEVICES AND METHODS

(71) Applicant: Joshua Aaron Schneider, Lincoln, NE (US)

(72) Inventor: Joshua Aaron Schneider, Lincoln, NE (US)

(73) Assignee: Joshua Aaron Schneider, Lincoln, NE (US)

( * ) Notice: Subject to any disclaimer, the term of this patent is extended or adjusted under 35 U.S.C. 154(b) by 928 days.

(21) Appl. No.: 17/232,965

(22) Filed: Apr. 16, 2021

(65) Prior Publication Data

US 2021/0321697 A1 Oct. 21, 2021

Related U.S. Application Data

(60) Provisional application No. 63/045,569, filed on Jun. 29, 2020, provisional application No. 63/010,981, filed on Apr. 16, 2020.

(51) Int. Cl.
| | |
|---|---|
| *A61K 9/70* | (2006.01) |
| *A41D 13/11* | (2006.01) |
| *A61L 9/20* | (2006.01) |
| *D06M 10/06* | (2006.01) |
| *D06M 11/45* | (2006.01) |
| *D06M 11/83* | (2006.01) |
| *D06M 23/10* | (2006.01) |
| *D06M 101/32* | (2006.01) |

(52) U.S. Cl.
CPC ............ *A41D 13/1192* (2013.01); *A61L 9/20* (2013.01); *D06M 10/06* (2013.01); *D06M 11/45* (2013.01); *D06M 11/83* (2013.01); *D06M 23/10* (2013.01); *A41D 2500/00* (2013.01); *A61L 2209/21* (2013.01); *D06M 2101/32* (2013.01)

(58) Field of Classification Search
None
See application file for complete search history.

(56) References Cited

FOREIGN PATENT DOCUMENTS

CN 108559495 A * 9/2018 ......... C09K 11/7792

* cited by examiner

*Primary Examiner* — Susan T Tran (57) ABSTRACT

A mask assembly having antimicrobial properties is provided. The mask is preferably worn on a user's face and it comprises a material layer, preferably a polyester fabric, and an applied emulsion or combination of chemical components (a silver containing stabilized solution and a phosphorescent compound). The combination provides enhanced antimicrobial properties in the mask via the silver containing stabilized solution and the phosphorescent compound, which emits a controlled field around the mask of microbe destroying UV-C radiation, preferably in the 200-290 nm wavelength range. The emulsion may be applied to other surfaces wherever antimicrobial properties are desired.

7 Claims, 10 Drawing Sheets

ANTIMICROBIAL UV-C EMITTING COMPOSITION FOR MASKS AND RELATED DEVICES AND METHODS

FIELD OF THE DISCLOSURE

The disclosure herein relates generally to antimicrobial emulsions, textiles, clothing, personal accessories, medical equipment, and medical treatments. More specifically, a preferred embodiment of the disclosure relates to a facial mask comprising an antimicrobial emulsion affixed thereon or impregnated therein. Another preferred embodiment of the disclosure relates to the antimicrobial compound or emulsion affixed to other surfaces or impregnated into other materials where antimicrobial properties are desired.

BACKGROUND

Prior art medical masks are made to be thrown away. These masks are generally not washable, reusable, and they are not custom capable. The masks create waste and great expense to the medical field and other industries that use masks for daily functions. Some embodiments of the disclosure solve this problem.

Additionally, viruses and bacteria survive and propagate on many surfaces, including masks. Current methods to sanitize such articles are limited by the steps and materials required to properly sanitize the surfaces. Many chemicals, compounds, and materials are only effective for a certain amount of time, they are not applicable to all target substrates and surfaces, and/or they do not sustain their germicidal properties for practical efficacy and use. Many prior art devices and methods use other means to sustain their germicidal properties, many of which are costly and harmful to the environment. Such means include batteries and other power sources that consume natural resources and cause pollution.

Accordingly, there is an unmet need in the art for an antimicrobial compound or emulsion that may be applied to or affixed to a surface or impregnated into a material where antimicrobial properties are desired, such as on a medical mask, such that germicidal, antimicrobial, and antiviral properties are sustained and rechargeable for an extended period of time without the use of an electrical charging means.

BRIEF SUMMARY OF THE DISCLOSURE

One embodiment includes a face mask including a first material layer that is breathable and opaque to UV-C radiation and has a first side for positioning toward a user's face; a second material layer that is breathable and has a second side, that, when the first material layer and the second material layer are fastened together, will face away from the user's face; an emulsion sublimated with the second side of the second material layer, the emulsion including: a silver containing antimicrobial component; and a phosphorescent component; wherein the combination of the silver containing antimicrobial component and the phosphorescent component emit UV-C radiation when and after exposure to a visible light source. The first material layer may include a polyester fabric. The second material may include a velour polyester fabric. The silver containing antimicrobial component may include a silver containing stabilized solution. The phosphorescent component may include strontium aluminate. The emulsion may also include silica.

Another embodiment includes a method for making a face mask that includes the steps of: selecting a first material layer that is opaque to UV-C radiation; fastening the first material layer to a second material layer such that the resulting mask has a first side configured to face a user's face and a second side configured to face away from the user's face; adding a silver containing antimicrobial component to the second side; adding a phosphorescent component to the second side; and sublimating the silver containing antimicrobial component and the phosphorescent component on the second side. The first material layer and the second material layer may be made of polyester. The silver containing antimicrobial component may include a silver containing stabilized solution. The phosphorescent component may include strontium aluminate. In some instances, the sublimating step may include heating the second side to between about 350 to 450 degrees F. (176 to 232 degrees C.) for 30 to 720 seconds at a pressure of 30 to 70 psig (207 to 483 kPa). In some instances, the sublimating step may include heating the second side to about 380 to 400 degrees F. (193 to 204 degrees C.) for 30 to 50 seconds at a pressure of 30 to 70 psig (207 to 483 kPa).

Another preferred embodiment of the disclosure is a method of forming and using a germicidal, antimicrobial, and/or antiviral emulsion of two compounds that can be applied or added to any surface, substrate, liquid, or electronic device/fixture where germicidal, antimicrobial, and antiviral properties are desired. This emulsion can be applied by any means necessary to bond it to such elements that are listed above. Such means would require specific applications of heat, time, pressure, and/or other substances or devices desired to improve emulsion bonding and efficacy on the aforementioned surfaces and elements. The emulsion of the two chemicals should be trapped or bonded to work and function properly, in order to sustain the efficacy and reliability of the emulsion application over extended time periods.

In a preferred embodiment of the disclosure, the emulsion is comprised of a silver containing stabilized solution and a plastisol-based glow paint preferably combined in a 1:1 to 1:6 ratio and applied to a surface. The silver containing stabilized solution exhibits antimicrobial properties and the emulsion irradiates UV-C light in the range of 200-290 nm that is suitable for the destruction of viruses and other microbes. The UV-C is irradiated approximately 3.5 inches from the surface of the mask and at approximately 200-290 nm wavelengths as a result of the emulsion, wherein the silver containing stabilized solution and glow paint are synergistically combined.

Another embodiment is a composition of matter including doped strontium aluminate; and stabilized silver in solution, wherein the ratio of the doped strontium aluminate to silver is between about 18,000:1 and 1600:1. In some embodiments, the doped strontium aluminate may make up at least about 5 percent of the composition. The stabilized silver in solution may include silver containing stabilized solution. The stabilized silver in solution may be 0.003 percent silver; less than 5 percent citric, gluconic, acetic, oxalic, hydroxyacetic acids or other stabilizing organic acid; and less than or equal to 94.997% water and inert ingredients. The doped strontium aluminate may include strontium aluminate; and at least one rare earth element. In some embodiments, the rare earth element may be from the lanthanide series. The at least one rare earth element may include at least one of europium and dysprosium. The doped strontium aluminate may have a particle size of between about 20 and about 45 microns.

Another embodiment includes a method for making the composition of matter that includes the steps of forming a combination of doped strontium aluminate and a stabilized silver component in a ratio of 18,000:1 to 1600:1 doped strontium aluminate:silver. The method may further include the step of heating the combination for 30-50 seconds at 350 to 450 degrees F. (176 to 232 degrees C.) at a pressure of 30 to 70 psig (207 to 483 kPa). The method may include combining silica with the doped strontium aluminate and the stabilized silver component. The doped strontium aluminate may include strontium aluminate and a rare earth element. The stabilized silver component may include silver stabilized in an organic acid. The method may also include mixing the combined doped strontium aluminate and the stabilized silver component until an emulsion is formed. The doped strontium aluminate may include strontium aluminate and at least one rare earth element.

Examples of the more important features of the disclosure have been summarized rather broadly in order that the detailed description thereof that follows may be better understood and in order that the contributions they represent to the art may be appreciated. There are, of course, additional features of the disclosure that will be described hereinafter and which will form the subject of the claims appended hereto.

DETAILED DESCRIPTION OF THE EMBODIMENTS

While the present disclosure may be susceptible to embodiment in different forms, there is described herein in detail, a specific embodiment with the understanding that the present disclosure is to be considered an exemplification of the principles of the disclosure and is not intended to limit the disclosure to that described herein.

Herein is disclosed a composition of matter that may be applied to surfaces and materials, such as fabrics, that can absorb visible light or light of non-UV-C wavelengths and re-emit the absorbed energy as UV-C radiation that is known to have antimicrobial and germicidal properties. UV-C radiation has been used to clean, sanitize, and heal living things and sanitize non-living things. Thus, the composition of matter can be used in masks, clothing, bedding, and other materials to make provide UV-C radiation in order to inactivate, weaken, or kill viruses, bacteria, and providing sanitization naturally from a light source. The composition of matter may be used to impart antimicrobial properties on structures, including, but not limited to, apparel, fabric, metal, masks, park benches, rooms, cleaning equipment, carpet, flooring, upholstery, paints, printing ink, sublimation ink, stickers, and other such things where it can be used to provide safety for multiple people, structures, and living/nonliving things.

Figure 1:
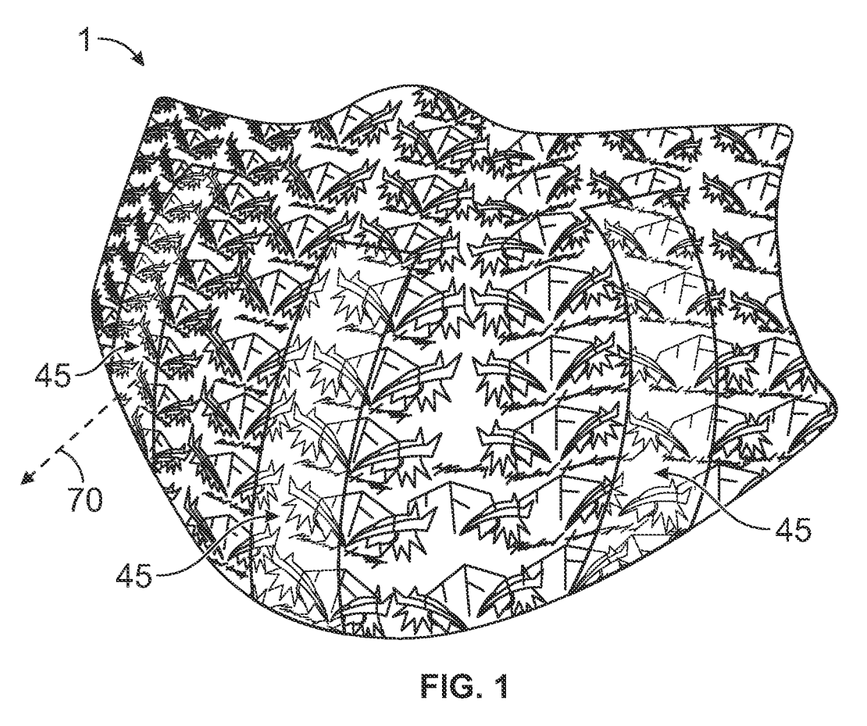
FIG. 1 is a front view of a facial mask with an ultraviolet emission layer according to one embodiment of the disclosure comprising a facial mask.
Figure 2:
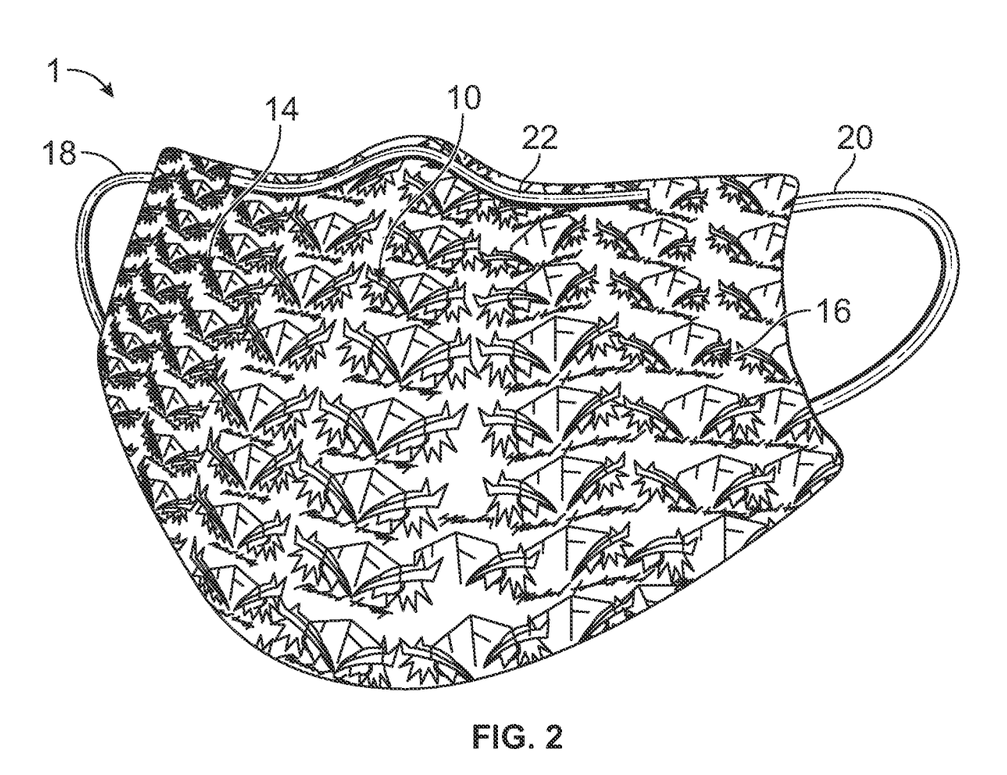
FIG. 2 is an alternative front view of a facial mask with an ultraviolet emission layer according to another embodiment of the present disclosure.
Figure 3:
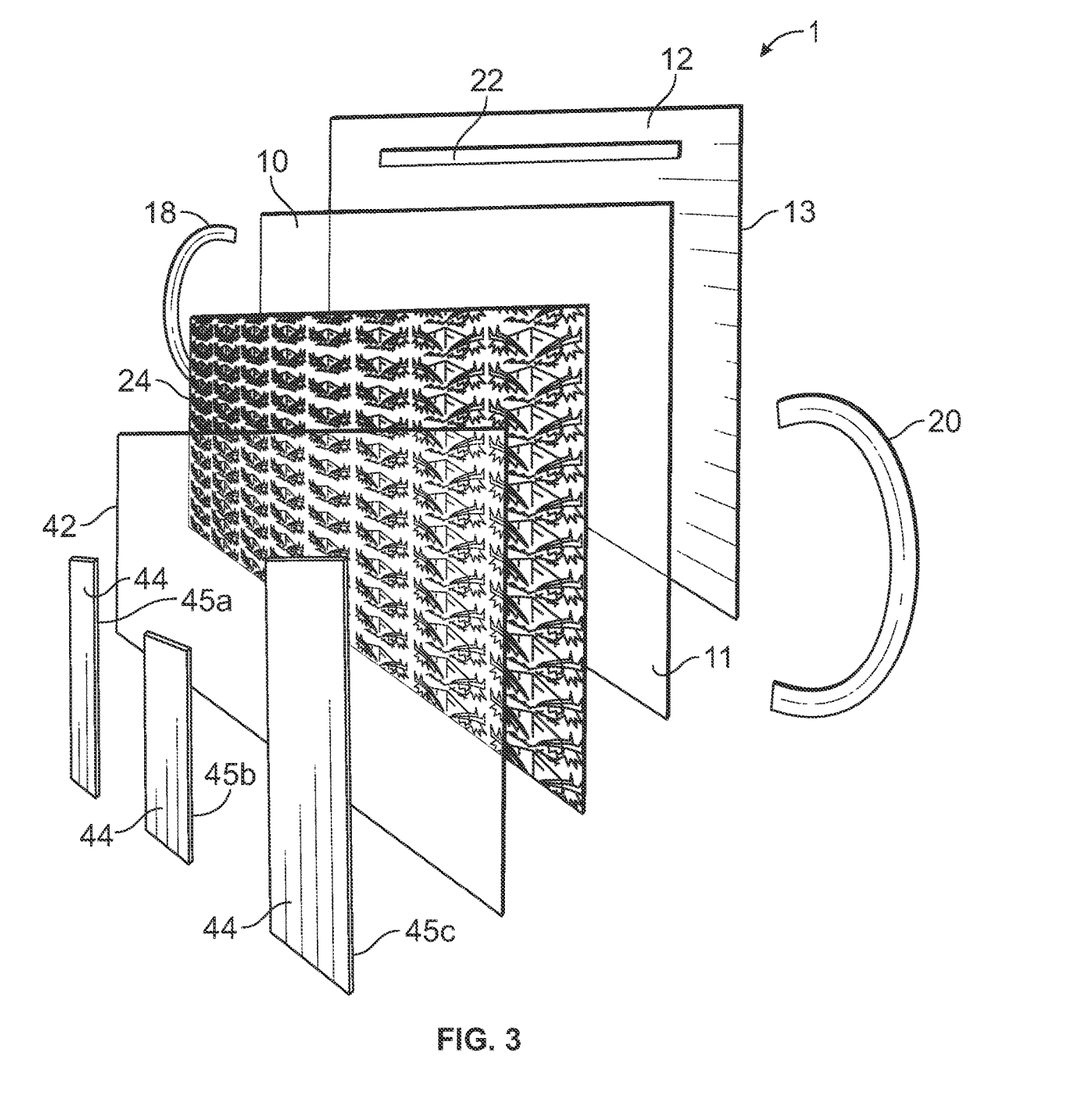
FIG. 3 is an exploded view of a one embodiment of a facial mask according to the present disclosure.

FIGS. 1-3 show embodiments of a wearable mask assembly 1 that is configured to be reusable while protecting a human user that include one or more strips 45 that emit ultraviolet radiation 70 in the C band (UV-C)

FIG. 2 shows the mask assembly 1 may include a material layer 10 sewn to a moisture wicking material layer 12 creating a first side gusset 14 and a second side gusset 16. The material layer 10 and/or the material layer 12 may be made of a fabric, such as, but not limited to, polyester. In some embodiments, the material layer 10 may be a velour knit fabric, for example a knit solid white velour, Product ID 1049-3161 18320 RN 35055 available from Joann's Fabrics. In some embodiments, the material layer 12 may be a moisture wicking fabric. For example, the material layer 12 may be polyester fabrics, such as, but not limited to, Procool® Performance Interlock Silver Coolmax Fabric available from Wazoodle Fabric in Bensalem, Pennsylvania. A first ear piece 18 may be sewn into the first side gusset 14. A second ear piece 20 may be sewn into the second side gusset 16. The ear pieces 18, 20 are optionally elastic. In operation, a human user may wrap the first elastic ear piece 18 around a first ear and the second elastic ear piece 20 around the second ear to protect the user. An optional elastic strap (not shown) may be used to connect the ear loop pieces 18, 20. This strap is sewn at each end around each separate ear loop piece 18, 20. The strap can be cut and made as desired.

In one embodiment, the material layer 10 can be made from a 10.5 inch by 7-inch 100 percent solid knit white velour fabric with size variations as needed by the user. The material layer 12 may be made from a 10.5 inch by 7-inch 100 percent polyester moisture wicking fabric with size variations as needed by the user. The elastic pieces for the ear loops 18, 20 can be any suitable stretchable fabric, such as two nylon/polyester pieces 18, 20 sewn between the material layers 10, 12 on either end for ear loops 18, 20 to be created the user. In some embodiments, a nose piece insert 22 can be placed in between another gusset 22 of the material layer 10 and be made of silver, aluminum, or other malleable alloy that is suitable material for use in a facial mask.

In some embodiments, the mask assembly 1 may be made into a diamond shape structure and completed as a blank. This allows the user to sublimate directly onto this mask 1, without having to sew the fabrics together afterwards. Prior to sublimation, the material layers 10, 12 may be sewn together, the ear loops 18, 20 already installed, but the unique shape and structure of the specific two material layers 10, 12 allows the person to sublimate onto the mask 1 directly with whatever design layer 24 is desired. The design layer 24 may have a flat shape structure and the material layer 12 may act as a border to the material layer 10 of the mask 1 and allow the design layer 24 to be put on via sublimation for a very clean look. The material layer 12 is configured to be facing the face of a user. Black trim of material layer 10 and/or material layer 12 does not accept the sublimation ink or allows it to be shown, thus creating an attractive trimmed look of the design layer 24 without the need of sewing the mask 1 afterwards. This can be done with or without a glow-in-the-dark paint 44 added (FIG. 3). This allows a user to have a blank mask 1 that is already structurally completed, and the ability to customize the mask 1 plus apply a design layer 24 via sublimation. This in turn allows the user to make a designed mask 1 in the matter of 45 seconds via heat press and text print sublimation paper, such as TexPrint® XPHR paper or TexPrint® R paper with a designed print on it via sublimation ink and sublimation printer. Said TexPrint® XPHR paper or TexPrint® R paper being available from Beaver Paper & Graphic Media, Inc., headquartered in Lawrenceville, GA. In some embodiments, the design layer 24 may include a silica infused sublimation paper as would be understood by a person of ordinary skill in the art.

FIG. 3 shows an exploded view of a mask 1 of FIG. 2 according to one embodiment of the present disclosure. The mask 1 may include the material layer 12 with a first side 13 configured for positioning toward the user's face. The material layer 10 may be disposed adjacent to the material layer 12 and opposite the first side 13. The material layer 10 may have a second side 11 that is facing away from the user's face. When the material layer 10, such as in a velour knit, has a softer side and a harder side, then the second side 11 may be the harder side. The material layer 12 and material layer 10 may be sown or otherwise affixed to one another such that the first side 13 and the second side 11 are facing opposite directions. An optional nose piece 22 may be disposed on one of or between the material layers 10, 12. In some embodiments, an optional sublimation design 24 may be deposited on the second side 11. A silver containing antimicrobial component 42 may be added to the material layer 10. Herein, the term "antimicrobial" describes any substance that is harmful or deadly to microbes, including antibacterial and antiviral substances. The antimicrobial component 42 may include a silver containing stabilized solution. In some embodiments, the silver containing stabilized solution, such as silver in citric acid, may be soaked into or otherwise permeate the material layer 10 through suitable application methods, including, but not limited to, spraying, brushing, sprinkling, and pouring. In some embodiments, the silver containing antimicrobial component 42 may be made of a mixture of about 0.003 percent Ag, less than 5 percent of one or more of citric, gluconic, acetic, oxalic, hydroxyacetic acids or other suitable stabilizing organic acid as would be understood by a person of ordinary skill in the art, and less than or equal to 94.997 percent water and inert ingredients, where the silver ions are electrically generated and stabilized by the at least one organic acid.

A phosphorescent component 44 may be added to the component 42 such that the silver containing antimicrobial component 42 and the phosphorescent component 44 are blended during the application process or when heat and pressure are applied. The phosphorescent component 44 may be applied continuous or discontinuous in its coverage of the material layer 10. For example, the phosphorescent component 44 may be applied at intervals of 3 inches apart in strips or stripes 45 that preferably run up and down (perpendicular) to the length of the mask second side 11. It is contemplated that the strips 45 may be provided in different shapes and orientations on the mask 1, and that a different number of strips or geometric configurations, such as dots, may be used. The first and last strip 45 of the blue glow paint 44 starts at 1 inch from the edge of the width of the second side 11 of the mask 1. Each strip 45 of blue paint 44 may be approximately 1.5 inches in width and may run to the border of the upper part of the front fabric layer 10. In some embodiments, there may be multiple, noncontiguous strips 45. There are preferably three total strips 45a, 45b, 45c that spaced horizontally, except that the middle strip 45b in the center of the mask 1 second side 11 stops at approximately 1.5 inches from the top part of the material layer 10. The lines of the phosphorescent component 44 do not have to run these exact dimensions. In some embodiments, spacing between two or more strips 45 may be based on the distance that the UV-C radiation emitted by the strips 45 is effective as an antimicrobial, thus reducing the need for the entire second side 11 to be covered by the phosphorescent component 44.

The phosphorescent component 44 includes a light emitting substance, such as, but not limited to, a phosphor for a glow-in-the-dark paint. In some embodiments, the phosphorescent component 44 may include Allureglow® USA Plastisol Glow PS-2045-BGB distributed by Allureglow USA in Rancho Cucamonga, California. In one embodiment, the phosphorescent component 44 may be made of doped strontium aluminate powder mixed with plastisol and 10-30% polymer resin. The doping agent may include one or more of europium, dysprosium, or other suitable doping agents known to those of ordinary skill in art. In some embodiments, the doping agent may be one or more rare earth elements. In some embodiments, the doping agent may be one or more lanthanide elements.

Figure 4:
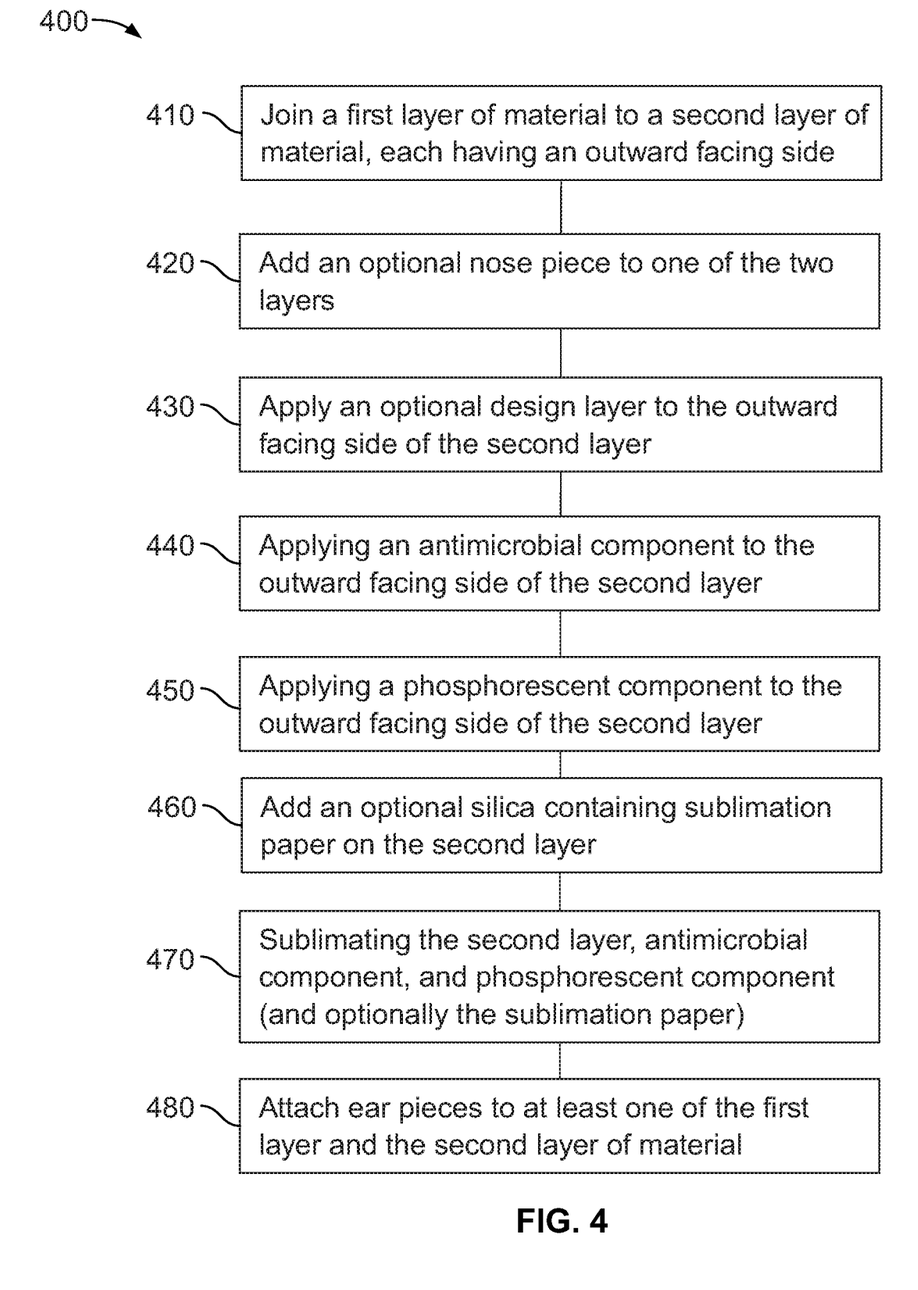
FIG. 4 is a flow chart of a method for making a facial mask according to the present disclosure.

FIG. 4 shows a method 400 for manufacturing the mask 1. In step 410, the material layer 12 and the material layer 10 may be overlaid and joined together. The joining of the material layers may include any suitable joining technique, including, but not limited to, gluing and stitching. The material layers 10, 12 may be sized based on the face of an intended user, such as a smaller size for children and a larger size for adults. In one embodiment, the dimensions may be 6.5"×9" for an adult or 4.5"×6" for a child, as shown in FIG. 2. In the event of stitching or sewing, the material layer 10 maybe pleated multiple times, such as three. Then pleating ends three times on the material layer 12 but in opposite direction the material layer 10. Pleats may be between 3 inches to 3.75 inches and are started 1.5 inches on either side of the mask 1 and on both material layers 10, 12. After that, the ear loop 18, 20 is installed (step 480) on the front right side on each end of the pleats making sure smooth side of ear loop 18, 20 is against the right side of the front 11 of the material layer 10. Next, preferably place the right sides of material layers 10, 12 together with the pleats facing each other, and sew a 0.25-inch seam around perimeter except top area off to a side. Subsequently, the mask 1 may be turned right side out and top stitch ⅛th inch around perimeter except at the nose piece 22 area in the middle of the mask 1. Then, preferably slope to ⅜th inch to insert nose piece 22, if desired. At the end of the nose piece 22 area one may insert a nose piece 22 and finish with a ⅛-inch closing opening. Finally, the nose piece 22 may be crimped to be shaped like the bridge of a nose, or the nose piece 22 may remain straight for the end user to bend as desired.

In step 420, an optional nose piece may be disposed on either the first side 13 or the second side 11. If the optional nose piece is disposed between the material layer 12 and the material layer 10, then this step may be performed prior to the joining in step 410. In step 430, the optional design layer 24 may be added to the second face 11 of the material layer 10. The design layer 24 may act as a masking layer. The addition of the design layer 24 may include heating the design layer 24 to affix it to the material layer 10. In some embodiments, the design layer 24 may include a pattern printed on sublimation paper by a sublimation printer using sublimation ink that can be applied by heating and pressing the design layer on the material layer 10. In step 440, the silver containing antimicrobial component 42 may be added to the material layer 10 on the second side 11. The silver containing antimicrobial component 42 may be applied by a suitable deposition technique, including spraying, sprinkling, brushing, pouring, and soaking. In step 450, the phosphorescent layer 44 may be added using any suitable technique used for step 440. In some embodiments, steps 440 and 450 may be performed in reverse order.

In step 460, an optional piece of silica containing sublimation paper may be disposed on top of the second side 11. In some embodiments, the silica is used. In step 470, the silver containing antimicrobial component 42 and the phosphorescent layer 44 and the optional sublimation paper may be sublimated to form a UV-C emission layer 45. The sublimation step may include the application of heat and pressure for a selected period of time to facilitate a chemical reaction between the silver containing antimicrobial component 42 and the phosphorescent layer 44. In some embodiments, the sublimation may include heating to a temperature of about 380 to 400 degrees F. (193 to 204 degrees C.) for 30-50 seconds while under a pressure of 30 to 70 psig (207 to 483 kPa). The temperature, time, and pressure may vary based on the composition of the material layer 10 and the components 42, 44 as would be understood by a person of skill in the art. In some embodiments, the temperature may be between about 350 and about 450 degrees F. In some embodiments, the selected time may be between about 30 seconds and about 12 minutes. In some embodiments, step 410 may be performed after any of steps 440-470. In some embodiments, the phosphorescent component 44 and the silver containing antimicrobial component 42 may be allowed to dry prior to step 470 being performed.

In step 480, ear pieces 18, 20 may be added to the mask 1. In some embodiments, step 470 may occur after any of the steps 410-450.

In operation, the sublimated emission layer 45 absorbs visible light and then reemits the energy received from the visible light as UV-C radiation 70. UV-C radiation 70 kills and breaks down viruses by interfering with the genetic material of the viruses. The emission process is gradual, as is the nature of the phosphorescent material, so that the emission layer 45 releases its stored energy as UV-C radiation of a period of time. The UV-C radiation is hostile to microbes, both viral and bacterial in nature, and acts to irradiate the microbes in proximity to the mask 1 resulting in their weakening and death. Separately, the silver containing antimicrobial component 42, on its own may kill, harm or inhibit the growth of bacteria or viruses, such as in the case of silver containing stabilized solution, but does not emit radiation as a mechanism for doing so. Prior to sublimation, the phosphorescent layer 44 only received and emits visible light, at varying wavelengths; however, this changes when at least some of the emissions are in the UV-C wavelengths after sublimation with the silver containing antimicrobial component 42 is performed. In some embodiments, the UV-C radiation may be sufficient to kill microbes at a range of about 3.5 inches (8.9 cm) from the material layer 10. It is contemplated that amendments to the emulsion 40 may provide for an irradiation distance that is greater than 3.5 inches, depending on where the emulsion 40 is applied. This UV-C frequency 70 (approximately 200-290 nm) is emitted for several hours after exposure to a light source, but with constant light shining on the mask 1 can continuously emit this level of UV-C. The best source of light to charge this mask 1 or other fabrics treated with this process is ultraviolet light, however it is not limited to this light source. This light source just gives the paint 44 the best charge and the fastest charge. This means that after charging, a person wearing the mask 1 will have viral protection for several hours. The silver containing antimicrobial component 42 of the mask 1 or other treated fabric is effective against some microbes without light or any sort of light source charging it. When exposed to light, the mask 1 has antimicrobial properties to any microbes that pass through the mask 1 and make contact with the silver containing antimicrobial component 42 and also to microbes in proximity to the UV-C emission strips 45 through irradiation.

The material layer 12 acts as a radiation barrier to protect the user's face from exposure to the UV-C, hence it is important that the material layer 12 have the property of blocking UV-C radiation.

In a specific example, sublimation of a combination of silver and citric acid in solution and PS-2045 BLUE glow paint may be performed after the two substances have been applied to a velour polyester fabric of a mask. The sublimation may involve heat pressing the fabric with the silver and citric acid in solution and PS-2045 BLUE glow paint at 400 degrees F. for approximately 45 seconds at 30 to 70 psig (207 to 483 kPa). In some embodiments the material layer 10 may play a role in the sublimation reaction. The material layer 10 is not limited to polyester, as other suitable fabrics may be used. By fixing the silver containing antimicrobial component 42 and the phosphorescent component 44 in the material 10, the product made of treated material 10 can washed, re-used, bleached, over and over again without losing any of the safety features provided via this process and unique structure of the mask and/or with this specific fabric that allows this unique development and safety feature to happen.

Figure 5:
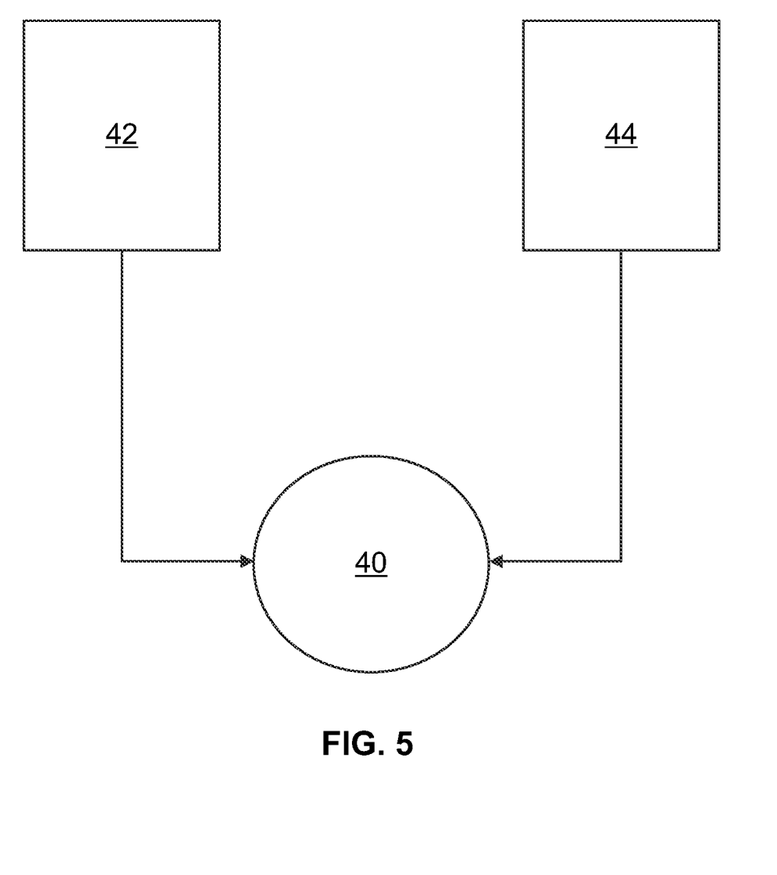
FIG. 5 is a diagram of an embodiment of an emulsion provided in accordance with the disclosure.

FIG. 5 shows a diagram of a process for making UV-C an emulsion 40 that, when heated and under pressure, may form a UV-C emission capacity material. The silver containing antimicrobial component 42 and the phosphorescent component 44 may be combined to form the emulsion 40. In some embodiments, the components 42, 44 may be mixed in a 1:1 to a 6:1 ratio (silver containing antimicrobial component in solution to phosphorescent component). In some embodiments, the phosphorescent component 44 may make up at least 15% of the emulsion 40. In one embodiment, the emulsion 40 may be made up of 15-50 percent PS-2045 and 50-85 percent silver containing stabilized solution. In another embodiment, the emulsion 40 may be made up of 15%-50% PS-2045, 50%-85% silver containing stabilized solution, and up to 10% silica.

The phosphorescent component 44 is a substance that emits light after exposure to an independent light source (e.g. reemission). An exemplar of the phosphorescent component 44 is PS-2045 BLUE paint; however, the phosphorescent component 44 is not limited to glow-in-the-dark paint. Any suitable light emitting material may be used such that it will bind with the silver containing antimicrobial component 42 (i.e. silver containing stabilized solution) and emit UV-C radiation after exposure to the independent light source. In some embodiments, the phosphorescent component 44 may be any phosphor emitting light in that may be stepped up or down to the UV-C range by the addition of the silver containing antimicrobial component 42, such as the phosphorescent powder used in glow-in-the-dark paint (i.e. strontium aluminate, zinc sulfide). The emulsion 40 may be applied to a material layer 10 and then sublimated using heat and pressure for a selected amount of time to produce a mask 1 with UV-C emitting capacity. The property of the UV-C emission capacity material is called a "capacity" since the material will not emit UV-C without exposure to an external light source to "charge" the material.

One method by which the emulsion 40 including silver containing stabilized solution 42 and blue glow paint 44 emits UV-C light 70 and is antimicrobial is by virtue of the crystal structure of the silver in the silver containing stabilized solution 42. This silver structure amplifies or magnifies the glow attribute to transition the normal UV-A and UV-B output levels that are seen in other glow-in-the-dark paint applications, to amplified UV-C levels 70 of 200-290 nm. The process of applying the emulsion onto different substrates and surfaces may be unique for each use application. The combination of the silver containing stabilized solution 42 and glow paint 44 causes emission of UV-C light 70 that irradiates microbes sufficiently to kill or weaken them up to a distance of approximately 3.5 inches from the mask 1.

Once the solid knit white velour 100% polyester fabric 10 is treated with the silver containing antimicrobial component 42 and the phosphorescent component 44, such as via the emulsion 40, it then goes into the next step of the process. This process is done much in the same matter as to the other glow element process that is stated in this construction of the mask 1 styles within this disclosure.

The material layer 10 may be treated with the silver containing antimicrobial component 42 and the phosphorescent component 44. A heat press and sublimation paper or parchment paper may be used to complete the process. The heat press can be set to 380 to 400 degrees F. (193 to 204 degrees C.). The treated material layer 10 may be laid onto the heat press with the treated second side 11 facing the user. The sublimation paper or parchment paper may then be placed down on top of the treated material layer 10. The heat press is moved down with a pressure of 30 to 70 psig (207 to 483 kPa) to lock it into place. The heat press may continuously apply 380 to 400 degrees F. (193 to 204 degrees C.) temperature and pressure to both paper and material layer 10 for approximately 45 seconds.

After this process is done, the material layer 10 may then be sewn into the material layer 12 and the mask 1 constructed from this point forward. The second side 11 of the material layer 10 of the mask 1 may display the visible phosphorescent material 44, modified or not modified by the design layer 24. A second side 13 of mask 1 contacts a user's face.

This process can be done to treat this second side 11 of material layer 10 into large quantities for which then can be used for others to sew or make many different materials and apparel items, not just limited to masks. Other uses may include, but are not limited to scrubs, aprons, bedsheets, linens, clothing, masks, and hats.

The process stated above can also be used with the other styles of masks or fabric-based items that are made with these material layers 10, 12. The process for the fashion or diamond mask shape can be done as one step when adding a custom design and does not need to be done beforehand onto the fabric. The processes and steps listed above can be used directly onto the blank mask product with the black trim outline and diamond shaped mask. Because of the mask 1 unique flat surface and black trim, the sublimation design, glow process, or emulsion process may be applied to this blank mask 1 product and completed without having to be first applied to the second side 11 of material layer 10 and then sewn as listed above.

In some embodiments, the mask 1 or any article including the material layer 10 (after treatment) combined with the material layer 12 may have the properties of being (1) antiviral for period of time after exposure to a visible light source, (2) antimicrobial permanently. The material layer 10 may also offer the properties of being sufficiently dense or water repellant to block moisture and not allow moisture to pass through, and, in the case of the mask 1, still allow air flow sufficient for breathing. The material layer 12 may also offer the property of blocking UV-C from the material layer 10. The material layer 12 may also wick moisture from the users face, act as a particle filter, Additionally, the mask 1 can comprise custom designs via sublimation that also are permanent and provide additional safety features; each style of mask 1 made with these specific layers can have glow in the dark capabilities; each style of mask 1 can be shaped, altered, or designed to suit the needs of any individual who needs or wants a mask 1; the mask 1 can be made to retain all these desirable features; and the emulsion 40 emulsion may provide flame retardancy and does not ignite with flame applied to the emulsion 40, making the emulsion 40 a great use for safety application of the mask 1 and the person wearing it. The mask 1 may have a diamond shape with fitted pockets on either side of the mask 1 or a pleated (such as three pleats on either side of the mask 1) structure.

In some embodiments, the emulsion 40 may be heated and exposed to pressure for a selected period of time to form a material with UV-C emission capacity independent of the material layer 10.

Figure 6:
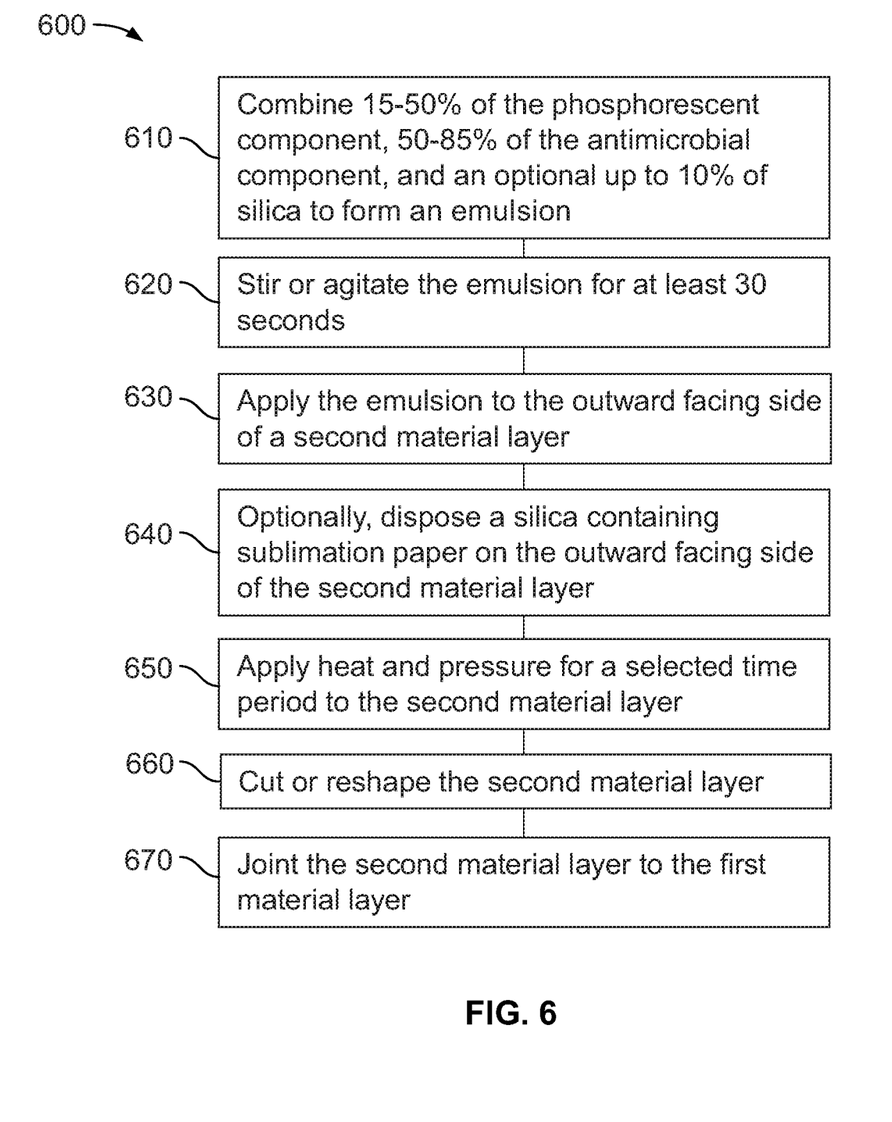
FIG. 6 is a flow chart of a method for forming a material with UV-C emitting properties according to one embodiment of the present disclosure.

FIG. 6 shows a flow chart of a method 600 for making a UV-C emulsion 40 and applying it. In step 610, 15-50% of the phosphorescent component 44, 50-85% of the silver containing antimicrobial component 42, and an optional up to 10% of silica are combined. In step 620, the phosphorescent component 44, the silver containing antimicrobial component 42, and optional silica are stirred or otherwise agitated until an emulsion 40 forms. This mixing step may take repeated mixing and latent periods. In step 630, the emulsion 40 may be applied to the second side 11 of the material layer 10 (regardless of whether the material layer 10 is integrated with the material layer 12). In step 640, an optional sublimation paper layer containing silica may be disposed on the second side 11. In step 650, heat and pressure are applied to the material layer 10, and optionally the sublimation paper, to sublimate the phosphorescent component 44, the silver containing antimicrobial component 42 and the optional silica onto the material layer 10. This step may include applying temperatures of about 380-400 degrees F. for about 30-50 seconds at a pressure of about 30 to 70 psig (207 to 483 kPa). In step 660, the material layer 10 may be cut or formed into a desired shape. In step 670, the material layer 10 may be joined to the material layer 12. In some embodiments, step 670 is optional. In some embodiments, steps 660 and 670 may be performed before or concurrent with step 610 or step 620.

Figure 7:
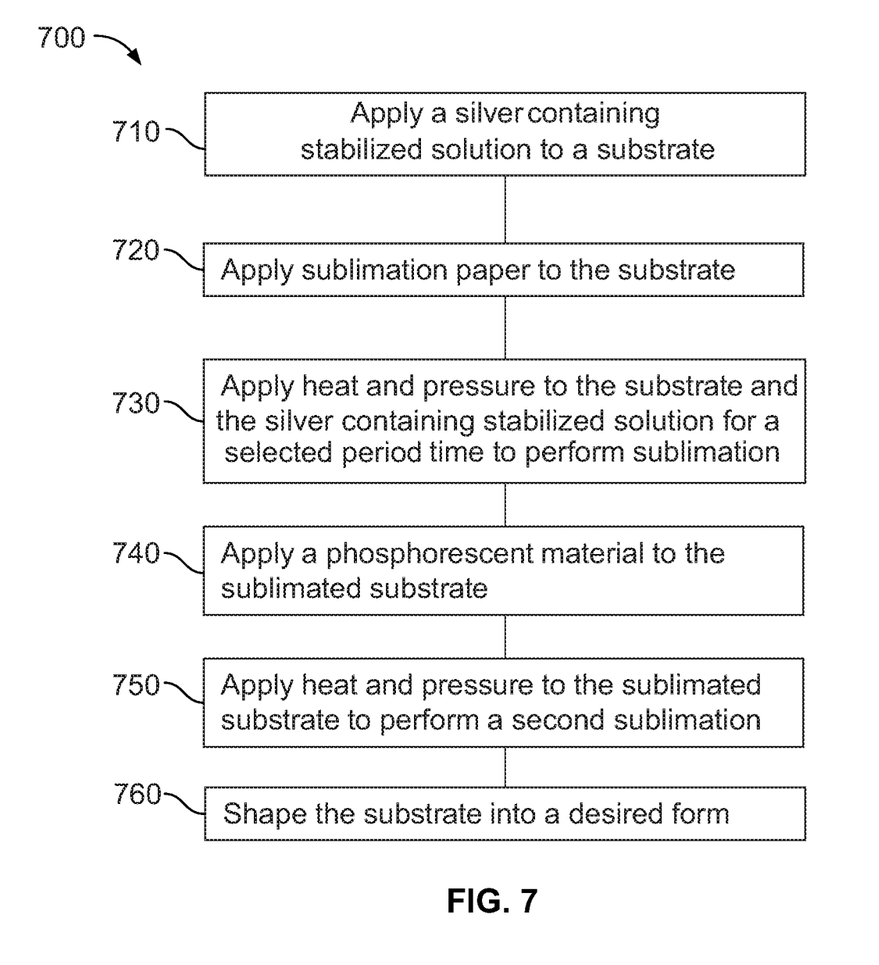
FIG. 7 is a flow chart another method for forming a material with UV-C emitting properties according to one embodiment of the present disclosure.

FIG. 7 shows a method 700 for making a fabric with UV-C radiation properties according to one embodiment of the present disclosure. In step 710, a silver containing stabilized solution may be applied to a substrate, such as material layer 10. In step 720, a silica containing sublimation paper, such as TexPrint XPHR paper, may be deposited on the second side 11 material layer 10. In step 730, the material layer 10, along with the sublimation paper and the silver containing stabilized solution may be sublimated through the application of 30 to 70 psig (207 to 483 kPa) and 380-400 degrees F. for 30-50 seconds. In step 740, a phosphorescent paint, or any suitable phosphor in a solution or mixture, such as Allureglow PS-2045, may be applied to the second side 11. In step 750, the treated material layer 10 may be sublimated through the application of 30 to 70 psig (207 to 483 kPa) and 380-400 degrees F. for 30-50 seconds. In step 760, the material layer 10 may be shaped as desired. In some embodiments, steps 760 may be performed before any of steps 710-750.

Figure 8:
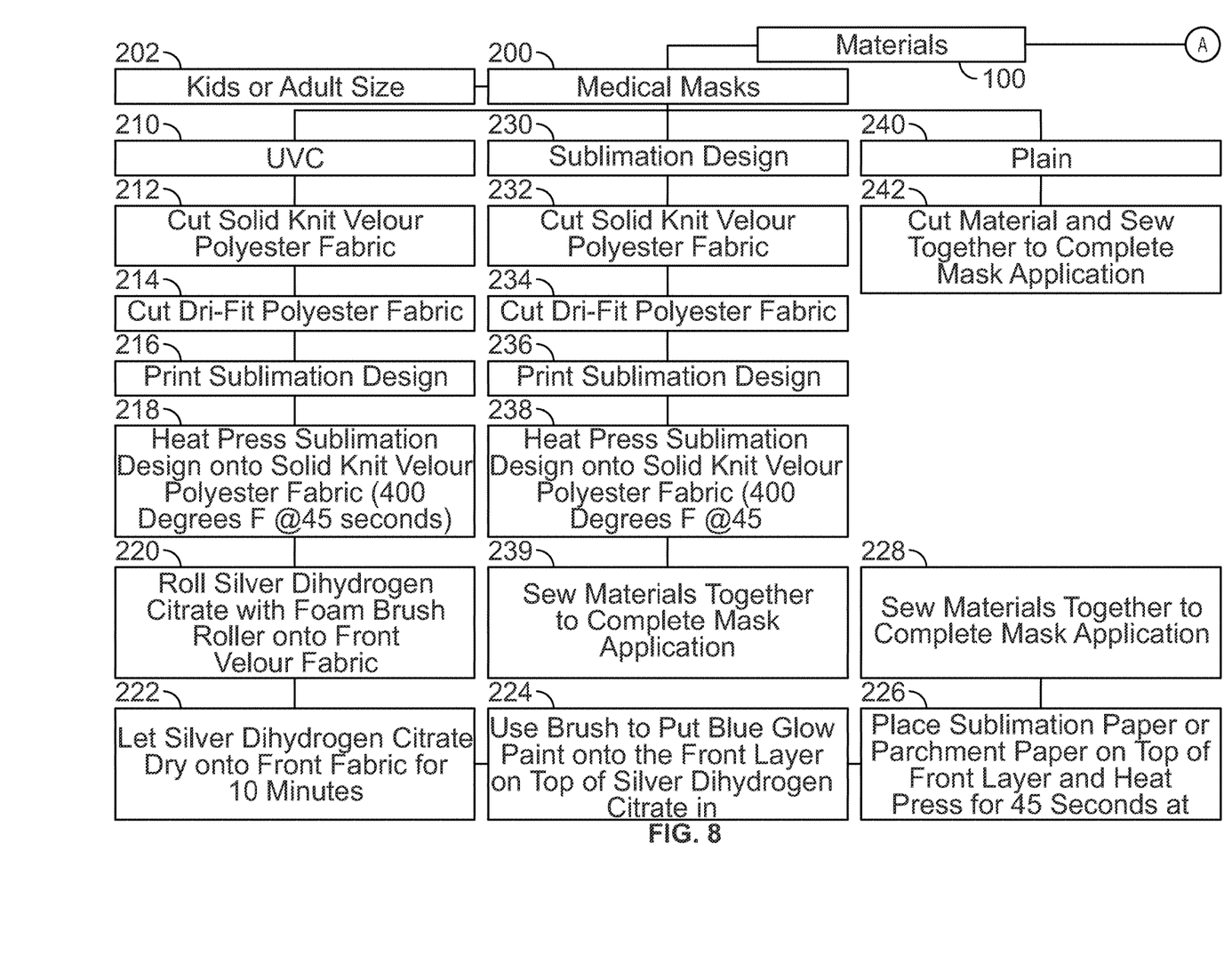
FIG. 8 is a flow chart showing a variety of masks manufacturing methods according to the present disclosure.

FIG. 8 shows a flow chart for making a variety of masks for a variety of uses according to present disclosure. Steps are provided for the manufacture of masks 1, 200, 300 provided in accordance with embodiments of the present disclosure.

First, materials 100 are selected for the material layers 10, 12, the silver containing antimicrobial component 42, the phosphorescent component 44, and the optional design pattern 24 and nose piece 22. Then, it is determined whether medical masks 200 or fashion masks 300 are desired. Additionally, a determination of size 202, 302 is made.

Medical masks 200 are divided into at least three categories, UV-C 210, sublimation design 230, and plain 240.

For UV-C masks 210: (i) step 212 is cutting a solid knit velour polyester fabric 10; (ii) step 214 is cutting a Dri-Fit® polyester fabric 12; (iii) step 216 is printing a sublimation design 24; (iv) step 218 is heat pressing the sublimation design 24 onto the solid knit velour polyester fabric 10 (at approximately 380-400 degrees F. for approximately 30-50 seconds); (v) step 220 is applying the silver containing stabilized solution 42 (i.e., with foam brush roller) onto front velour fabric 10; (vi) step 222 is letting the silver containing stabilized solution 42 dry on the front fabric 10 for up to 10 minutes; (vii) step 224 is using an applicator to apply blue glow paint 44 onto the second side 11 on top of the silver containing stabilized solution 42 in designated areas (i.e., strips 45) as desired; (viii) step 226 is placing sublimation paper or parchment paper on top of second side 11 and applying the heat press for approximately 30-50 seconds at approximately 380-400 degrees F.; and (ix) step 228 is sewing materials together to complete the mask 1, 210.

For Sublimation Design masks 230: steps 232, 234, 236, 238, and 239 are the same as steps 212, 214, 216, 218, and 228, respectively, to form mask 230.

For Plain masks 240, step 242 is cutting materials and sewing them together to complete mask 240.

Fashion masks 300 are divided into at least three categories, glow-in-the-dark 310, sublimation design 320, and plain 330.

For Glow-in-the-Dark masks 310: (i) step 312 is painting a glow-in-the-dark paint 44 onto second side 11 of a completed mask; (ii) step 314 is heat pressing sublimation paper onto the side 11 with paint 44 side up (at approximately 380 to 400 degrees F. (193 to 204 degrees C.) for approximately 30-50 seconds); (iii) step 316 is determining whether a design 24 will be added; (iv) step 317 is, if design 24 is desired, printing design 24 and then heat pressing design 24 onto the layer 11; (v) step 318 is heat pressing the design 24 at approximately 380 to 400 degrees F. (193 to 204 degrees C.) for approximately 30-50 seconds; and (vi) step 319 is providing a completed mask 310.

For Sublimation Design masks 320: (i) step 322 is printing a sublimation design 24; (ii) step 324 is heat pressing the design 24 onto mask 320 with design 24 facing down on second side 10; (iii) step 326 is heat pressing the design 24 at approximately 380 to 400 degrees F. (193 to 204 degrees C.) for approximately 30-50 seconds; and (iv) step 328 is providing a completed mask 320.

For Plain masks 330, step 332 is forming a completed mask 330 and step 334 is allowing consumers and businesses to apply their own custom designs for customers by using the mask 300 and applying a sublimation printing and heat pressing process to form mask 330.

In some embodiments, not every respective step in every FIG. 4 process is required to form masks 210, 230, 240, 310, 320, 330, the order of certain steps may be interchangeable, and the detail of each step is merely exemplary.

Generally, the emulsion 40 is beneficial because it will help the world be healthier, provide preventative measures to limit transmission of viruses and bacteria, and provide a solution to halt the spread of infectious diseases, cancers, and can be used to provide treatment measures for an overall healthier output for anything living/nonliving. Using the emulsion 40 that can absorb light naturally and emits UV-C radiation 70 provides a solution for an easy way to provide safety. Surfaces and substrates are constantly sanitized, self-cleaning with light source transmission onto them, and help many businesses work in a safe environment. The emulsion 40 allows businesses to work faster and more efficiently, especially in the healthcare industry. This emulsion 40 can be used on any surface/substrate and applied internally/externally with any means necessary to make more permanent or semi-permanent onto such substrates/surfaces.

Masks 1 comprising emulsion 40 and/or other variable elements have been tested as follows.

Filterability and Breathability: While pulling a vacuum through the fabric, different test fabrics were compared on bases of flow percentage through the fabric (0-100%). First tests were conducted at 2+/−0.2 psi (~1406 mmH2O or ~103 mmHg) and subsequent tests were conducted at 5+/−0.2 psi (~3515 mmH2O or ~259 mmHg). A control variable of an N-95, 3M® NIOSH tested mask without valve was used. Experimental variables comprised mask 1, namely, a 1-ply mask 1, a 2-ply mask 1, both with and without treatment of the emulsion 40. Results were reported in percentage of resistance to flow to represent breathability of the masks (reciprocal of percentage flow relates to filterability).

Microbial Resistance: Using petri dishes of tryptic soy both (total bacteria), test fabrics were swabbed and plated, incubating at 42+/−0.8 F without light exposure and at standard 45+/−2% relative humidity. Fabrics were compared on basis of initial growth and subsequent growth through the incubation period, before and after exposure to UV light. The first test incorporated 15 seconds exposure of UV, on the treated surface. Subsequent tests were at 45 seconds and 10 minutes and at 3.5 inches from the treated surface. The control was a mask 1, 1-ply, polyester, untreated mask 1, swabbed and plated as received. Experimental variables were various treatments on fabric. Plates were checked at 72 hours for total bacteria within 1 hour of target check. Results were noted in number of visible colonies after an incubation period.

UV-C Range of Secondary Emission: Fabric was tested using a single beam, UV-VIS spectrometer, shutting off the light source and instead using the secondary emission of light from the mask. The first step was to subject the mask to both ambient fluorescent light and specifically time the exposure of UV-A light at 365 nm. The second step was to capture resulting secondary emission of light from mask. A detector was set to specific wavelengths in the UV range (202-350 nm) in increments of 2 nm. Once the wavelength of secondary emission was determined, measurements were taken by re-exposing the fabric to the UV-A light at 365 nm for the time specified. After exposure, the fabric was set into the sample cell. Controls were both set from no added UV light exposure and untreated fabric. Experimental variables were various treatment methods and products provided in connection with the disclosure. Results are reported in % T (inverse of adsorption %), to the nearest 1%.

The filterability of mask 1 is comparable to the NIOSH tested N95 masks on air flow. However, as a double ply mask 1, they will block direct contact of droplets/mist to directly and instantly contact the areas covered by the person wearing it. Further, this mask 1 will keep the person wearing it from touching their hands to their nose and mouth, which is among the largest of concerns by the CDC.

Further, nothing grew on the S masks (either way it was applied) and subsequent swabs, incubated on tryptic soy broth plates. Comparing to the non-S variable, the mask is antimicrobial to those organisms it was exposed to during the making, shipping, handling and testing. That is significant. Since the route of entry is a major concern by the CDC, this mask did not allow any microbial growth, which could compromise a person fighting additional bacterial contact.

When the phosphorescent component 44 is exposed to light, it will emit within the UV-C frequency range, even 3.5 inches away. The low-level UV-C, secondary emission from these masks was not isolated to the primary light charging it. Fluorescent and UV-A primary sources of light charged the coating, which then emitted its own frequency of UV-C light, independent of the primary source.

The medical community utilizes ASTM F2100-11 testing for certifying surgical masks, and non-surgical masks can relate to it. The tests performed in the initial qualification for mask 1 materials are relatable to the first four tests contained in ASTM F2100-11. The mask 1 comprises: (1) BFE (bacterial filtration efficiency), which relates to relates to the size of the holes in the fabric to create resistance to flow and capture of droplets containing micro-organisms and viruses. The N-95 and N-99 masks have what the FDA considers "passing standard" in ranking system of "low, medium and high" filtration; (2) PFE (particle filtration efficiency), which also relates to the size of the holes in the fabric to create resistance to flow and capture of particles through filtration; (3) Fluid Resistance as a direct function of the test to determine levels of BFE; (4) a Delta Pressure Differential that is related to the resistance to flowability versus breathability; (5) Flame Retardancy; and (6) Skin sensitivity.

Figure 9:
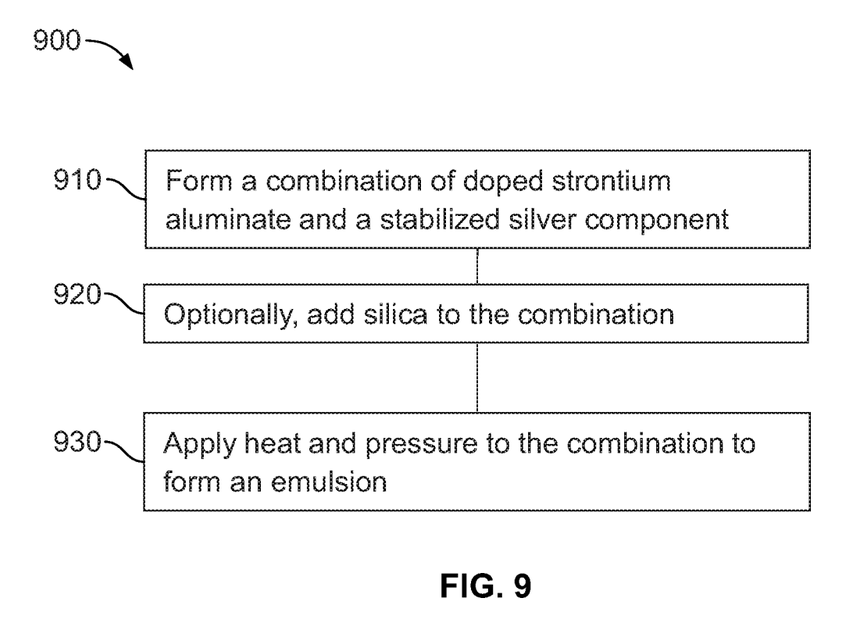
FIG. 9 is a flow chart showing a method of making a composition of matter with UV-C emitting capacity according to the present disclosure.

FIG. 9 shows a method 900 of making a composition of matter with UV-C emitting capacity according to one embodiment of the present disclosure. In step 910, the phosphorescent component 44 may be combined with a silver containing component, with or without its own antimicrobial properties, to form an emulsion that can be used to emit UV-C radiation after exposure to visible light. In some embodiments, the emulsion may be formed by mixing. The composition may include doped strontium aluminate and a stabilized silver component, of which silver in an organic acid is an example. The doped strontium aluminate may be doped with a rare earth, such as, but not limited to, europium and/or dysprosium. The ratio of the doped strontium aluminate and the silver in the stabilized silver component may be between about 18,000:1 to about 1600:1. In some embodiments, the doped strontium aluminate makes up at least 5 percent of the emulsion. In some embodiments, the doped strontium aluminate is a particulate with particles sized between 20 and 45 micrometers. In some embodiments, the stabilized silver component may be made up of about 0.003 percent silver, less than 5 percent of at least one of citric, gluconic, acetic, oxalic, hydroxyacetic acids or other suitable stabilizing organic acid as would be understood by a person of ordinary skill in the art, and a balance of less than or equal to 94.997 percent water and inert ingredients. "Stabilized" refers to a substance having its surface activity reduced or slowed to reduce or eliminate chemical interaction of the substance with its environment, thus halting degradation or reactivity, as would be understood by a person of ordinary skill in the art. In one embodiment, the emulsion 40 may be made by mixing doped strontium aluminate and a stabilized silver component in the ranges described above. In step 920, silica may be optionally mixed in into the combination. The silica may make up to 10 percent of the combination in some embodiments. In step 930, the combination may be processed using heat and pressure to form the emulsion 40. The conversion from the combination to the emulsion 40 may include heating the combination for 30-50 second at 350 to 450 degrees F. (176 to 232 degrees C.) at a pressure of 30 to 70 psig (207 to 483 kPa). The combination can be prepared and stored or processed into the emulsion 40 prior to distribution or application to a material, such as fabric. The emission of UV-C will only take place after the emulsion 40 is both processed (exposed to heat and pressure for the prescribed amount of time) and exposed to visible light to charge the emulsion 40.

What is claimed is:

1. A method of making a UV-C emitting emulsion comprising:
   mixing a combination of doped strontium aluminate and a stabilized silver solution in a ratio of 18000:1 to 1600:1 of doped strontium aluminate:stabilized silver solution to form an emulsion;
   adding silica to the emulsion to form a mixture; and
   heating the mixture for 30-50 seconds at 350° F. to 450° F. (176° C. to 232° C.) at a pressure of 30 psig to 70 psig (207 kPa to 483 kPa).

2. The method of claim 1, wherein the doped strontium aluminate comprises strontium aluminate and a rare earth element.

3. The method of claim 1, wherein the stabilized silver solution comprises silver stabilized in at least one organic acid.

4. The method of claim 1, where the doped strontium aluminate comprises strontium aluminate and at least one rare earth element.

5. A face mask comprising:
   a first material layer that is breathable and opaque to UV-C radiation and has a first side for positioning toward a user's face; and
   a second material layer that is breathable and has a second side, that, when the first material layer and the second material layer are fastened together, will face away from the user's face;
   wherein the second side of the second material layer is sublimated with the UV-C emitting emulsion of claim 1, and
   wherein the UV-C emulsion emits UV-C radiation when and after exposure to a visible light source.

6. The face mask of claim 5, wherein the first material layer comprises a polyester fabric.

7. The face mask of claim 5, wherein the second material layer comprises a velour polyester fabric.

* * * * *